United States Patent
Alford et al.

(10) Patent No.: US 6,677,150 B2
(45) Date of Patent: Jan. 13, 2004

(54) ORGAN PRESERVATION APPARATUS AND METHODS

(75) Inventors: Marlin L. Alford, Dublin, TX (US); Robert M. Dowben, Providence, RI (US)

(73) Assignee: Organ Transport Systems, Inc., Houston, TX (US)

(*) Notice: Subject to any disclaimer, the term of this patent is extended or adjusted under 35 U.S.C. 154(b) by 0 days.

(21) Appl. No.: 09/953,338

(22) Filed: Sep. 14, 2001

(65) Prior Publication Data
US 2003/0054540 A1 Mar. 20, 2003

(51) Int. Cl.[7] .............................................. A01N 1/00
(52) U.S. Cl. .............................. 435/284.1; 435/286.5; 435/286.6
(58) Field of Search ..................... 435/284.1, 286.5, 435/286.6, 1.2; 128/202.12; 604/41, 43, 44

(56) References Cited

U.S. PATENT DOCUMENTS

| | | | |
|---|---|---|---|
| 3,772,153 A | * 11/1973 | De Roissart | 435/284.1 |
| 3,881,990 A | 5/1975 | Burton et al. | 195/1.7 |
| 3,914,954 A | 10/1975 | Doerig | 62/306 |
| 3,995,444 A | 12/1976 | Clark et al. | 52/306 |
| 4,186,565 A | 2/1980 | Toledo-Pereyra | 62/306 |
| 5,051,352 A | 9/1991 | Martindale et al. | 435/1 |
| 5,326,706 A | 7/1994 | Yland et al. | 435/283 |
| 5,356,771 A | 10/1994 | O'Dell | 435/1 |
| 5,362,622 A | 11/1994 | O'Dell et al. | 435/1 |
| 5,385,821 A | 1/1995 | O'Dell et al. | 435/1 |
| 5,472,876 A | 12/1995 | Fahy | 435/284.1 |
| 5,476,763 A | 12/1995 | Bacchi et al. | 435/284.1 |
| 5,586,438 A | 12/1996 | Fahy | 62/78 |
| 5,807,737 A | 9/1998 | Schill et al. | 435/284.1 |
| 5,856,081 A | 1/1999 | Fahy | 435/1.2 |
| 5,965,433 A | 10/1999 | Gardetto et al. | 435/284.1 |
| 6,046,046 A | 4/2000 | Hassanein | 435/284.1 |
| 6,100,082 A | 8/2000 | Hassanein | 435/284.1 |

OTHER PUBLICATIONS

MAKROLON® Rx–1805 Polycarbonate Resin Lipid–Resistant, Radiation–Stabilized Medical Grade, Bayer Corporation.

* cited by examiner

Primary Examiner—David A. Redding
(74) Attorney, Agent, or Firm—McAndrews, Held & Malloy, Ltd.

(57) ABSTRACT

This invention is a transportable organ preservation system which substantially increases the time during which the organ can be maintained viable for successful implantation into a human recipient. A chilled oxygenated nutrient solution is pumped through the vascular bed of the organ after excision of the organ from the donor and during transport. The device of the present invention uses flexible permeable tubing to oxygenate the perfusion fluid while the $CO_2$ produced by the organ diffuses out of the perfusion fluid. One pressurized two liter "C" cylinder that contains 255 liters of oxygen at standard temperature and pressure can supply oxygen for up to 34 hours of perfusion time. The device uses a simple electric pump driven by a storage battery to circulate the perfusion fluid through the organ being transported. The vessel containing the organ to be transported is held at 4° C. by coolant blocks.

25 Claims, 6 Drawing Sheets

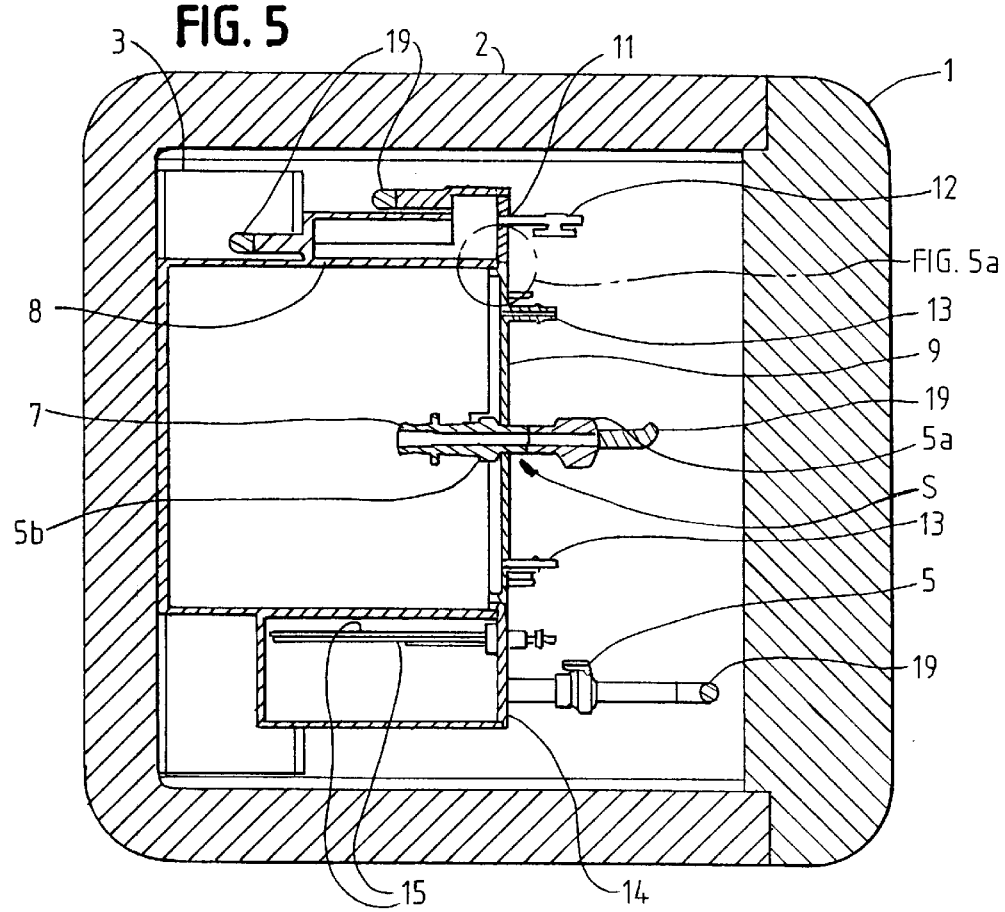
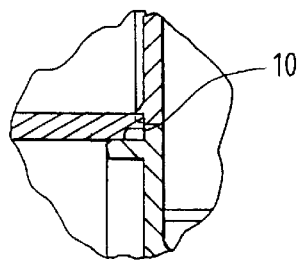
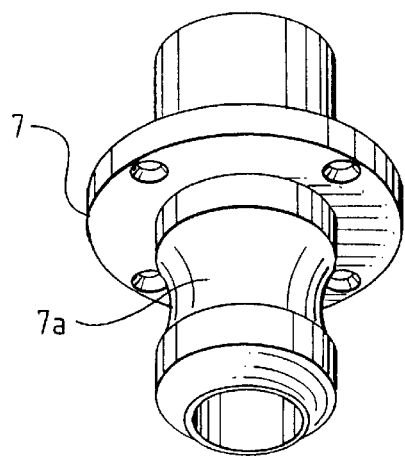

ORGAN PRESERVATION APPARATUS AND METHODS

CROSS-REFERENCE TO RELATED APPLICATIONS

STATEMENT REGARDING FEDERALLY SPONSORED RESEARCH OR DEVELOPMENT

FIELD OF THE INVENTION

This invention relates to a transportable organ preservation system and more particularly to a preservation system which substantially increases the time enroute during which the organ can be maintained viable for successful implantation into a human recipient. A chilled oxygenated nutrient solution is pumped through the vascular bed of the organ after excision of the organ from the donor and during transport.

BACKGROUND OF THE INVENTION

The surgical transplantation of organs has been successfully performed since 1960 owing to the improvement of surgical techniques, the introduction of by-pass circulation and the development of drugs that suppress immune rejection of the donor organ. At the present time, the donor organ is harvested under sterile conditions, cooled to about 4° C. and placed in a plastic bag submerged in a buffered salt solution containing nutrients, and finally transplanted into the recipient. The solution is not oxygenated and is not perfused through the organ blood vessels.

The lack of donor organ availability, particularly hearts, lungs, and livers, is a limiting factor for the number of organ transplants that can be performed. At the present time, less than 25% of patients who require a heart transplant receive a new heart, and less than 10% of patients who require a lung transplant receive one. A major consideration is the length of time that a donor organ will remain viable after it is harvested until the transplant surgery is completed. For hearts, this interval is about four hours. The donor heart must be harvested, transported to the recipient, and the transplant surgery completed within this time limit. Thus, donor hearts can be used only if they are harvested at a site close to the location where the transplant surgery will take place.

It has long been known that organs will survive ex vivo for a longer time if they are cooled to 4° C. and actively perfused through their vascular beds with a buffered salt solution containing nutrients, and that ex vivo survival of an isolated organ can be further extended if the solution is oxygenated. Several factors play a role in the prolonged survival. At 4° C. the metabolism is greatly reduced, lowering the requirements for nutrients and oxygen, and the production of lactic acid and other toxic end products of metabolism are also greatly reduced. Circulation of the perfusion fluid replenishes the oxygen and nutrients available to the tissue, and removes the lactic acid and other toxic metabolites. The buffered solution maintains the pH and tonic strength of the tissue close to physiological.

Perfusion that allows the transport of a harvested organ from a site removed from the location where the transplant surgery will be carried out requires the use of a light weight portable device that operates under sterile conditions for pumping the cold buffered nutrient salt solution through the organ blood vessels, and in which the organ also can be transported from the site of harvesting to the site of transplantation. In order for one person to carry the entire assembly without assistance, and to transport it in an auto or airplane, it should be compact, sturdy and light weight. The system for loading the perfusion fluid should be simple and allow minimal spillage. There must be a means for oxygenating the perfusion fluid. The device requires a pump with a variably adjustable pumping rate, which pumps at a steady rate once adjusted. Sterility must be maintained. To be completely portable, the device should contain a source of oxygen, an energy source to operate the pump, and should be housed in an insulated water tight container that can be loaded with ice. An entirely satisfactory device is not currently available.

The use of a light weight, cooled, self-contained perfusion device would have a number of beneficial consequences. (1) The organs would be in better physiological condition at the time of transplantation. (2) Prolonging the survival time of donor organs will enlarge the pool of available organs by allowing organs to be harvested at a distance from the site of the transplant surgery in spite of a longer transport time. (3) It would allow more time for testing to rule out infection of the donor, for example with AIDS, hepatitis-C, herpes, or other viral or bacterial diseases. (4) The pressure on transplant surgeons to complete the transplant procedure within a short time frame would be eased. Transplant surgeons are often faced with unexpected surgical complications that prolong the time of surgery. (5) Better preservation of the integrity of the heart and the endothelium of the coronary arteries at the time of transplantation may also lessen the incidence and severity of post-transplantation coronary artery disease.

On Oct. 12, 1999 the assignee of the present invention was granted U.S. Pat. No. 5,965,433 for a portable organ profusion/oxygenation module which employed mechanically linked dual pumps and mechanically actuated flow control for pulsatile cycling of oxygenated perfusate.

The aforementioned patent contains an excellent description of the state of the art in the mid-nineties and the problems associated with transport systems for human organs. The patent also outlines the many advantages obtained by the ability to extend the transport time from approximately 4 to 24 hours.

Human organ transplantation is plagued by limitations due to insufficient time to transport an organ while maintaining its viability and by an inadequate donor pool. The present invention will significantly diminish the problem of limited transport time by providing an apparatus which will extend the transport time to up to 48 hours. This increased time will inherently increase the size of the donor pool and will allow for extensive disease testing and matching.

The present invention will also greatly reduce damage to the organ being transported and will allow organs from post-mortem donors to be used. Today, organs are only harvested from donors who are brain-dead but whose organs have never ceased to function.

Currently, an organ is transported by putting the organ in a plastic bag of storage fluid, put on ice inside a cooler. In 4 hours, 12% of the transported organs "die" or become unusable, and all the organs are degraded.

A particular advantage of the transport system of the present invention is that it is easily loaded and unloaded by double-gloved surgical personnel and that the fittings require minimal dexterity to assemble and disassemble.

Another advantage of the present invention is that it does not use the flexible permeable membrane of the prior art which due to their constant flexing are subject to fatigue stresses and rupture with catastrophic results.

DESCRIPTION OF THE PRIOR ART

For the thirty-year history of organ transplantation surgery, maintaining the quality and viability of the organ has been an enormous challenge. The current method of transport, called topical hypothermia (chilling the organ in a cooler), leaves 12% of organs unusable because of their deteriorated physiological condition. Thousands of people die each year while on an ever-expanding waiting list. The need is great for a truly portable device that nurtures and oxygenates the organ throughout the entire ex-vivo transport.

Currently, when hearts, lungs, liver and certain other organs are harvested from a donor, medical teams have about 4 hours to transplant the harvested organ into the recipient. Damage to the organ at the cellular level occurs even during this short period.

Hypothermic, oxygenated perfusion devices are known in the art and have proven successful in maintaining viability of a human heart for 24 hours ex vivo in laboratory settings. While different devices are available for laboratory use under constant supervision, none are truly independently functioning and portable. For example, Gardetto et al., U.S. Pat. No. 5,965,433 describes an oxygen driven dual pump system with a claimed operating capacity of 24 hours using a single a 250 liter oxygen bottle. The intent of this device was to provide a user-friendly device that would be "hands off" after the organ was placed in the unit. Four major problems were evident. (1) The unit contains no bubble trap and removing bubbles is difficult and time consuming. (2) The lubricant in the pumps dries out after 10 or fewer hours of operation and the pumps stop. (3) At lower atmospheric pressure such as in an aircraft in flight, the pump cycles rapidly due to the reduced resistance to pumping, risking the development of edema in the perfused organ; and (4) Two bottles of oxygen failed to produce more than 16 hours of steady operation.

Doerig U.S. Pat. No. 3,914,954 describes an electrically driven apparatus in which the perfusate is exposed to the atmosphere, breaking the sterility barrier. It must be operated upright, consumes oxygen at high rates, and is heavy. The requirement for electric power and the necessity for a portable source of electric power severely limit the portability of this unit.

O'Dell et al., U.S. Pat. No. 5,362,622, U.S. Pat. No. 5,385,821, and O'Dell U.S. Pat. No. 5,356,771 describe an organ perfusion system using a fluidic logic device or a gas pressure driven ventilator to cyclically deliver gas to a sealed chamber connected to the top of the organ canister. Cyclical delivery of gas under pressure to the upper sealed chamber serves to displace a semi-permeable membrane mounted between the gas chamber and the organ canister. Cyclical membrane displacement acts to transduce the gas pressure into fluid displacement on the opposite side, providing flow of the perfusing solution.

The membrane is chosen for its permeability to gas but not to water. This permits oxygen to flow through the membrane to oxygenate the fluid and vent carbon dioxide from the fluid. The intent of such devices is to provide a system that uses no electricity, uses low gas pressure to achieve perfusate flow, has few moving parts, provides oxygenation of the fluid, can be operated in a non-upright position, isolates the organ and perfusate from the atmosphere, is of compact size and low weight to be portable.

While these systems may work in experimental settings, they fail to meet criteria claimed by the developers. For example, the amount of oxygen necessary to cycle the membrane is very large. When calculated over a 24 hour period, it would require 4 large tanks of oxygen to assure continuous operation. This amount of oxygen fails to meet the definition of portable. The pressure and volume of oxygen required to cycle the membrane is sufficient to cause tearing of the membrane or displacing it from its margins. Either of these occurrences would be catastrophic to the organ. The manner in which fluid is cycled into the organ chamber attempts to perfuse both within and around the organ, providing freshly oxygenated fluid to infiltrate and surround the organ. This procedure is without physiological basis since normally, oxygenation is achieved by oxygen diffusion outward from the organ's vascular bed.

All of these devices use a permeable membrane permeable to gas but not to water so that oxygen or other gas mixtures can be driven through the membrane into the perfusate and can vent $CO_2$, produced by the organ, from the perfusate.

The successful use of permeable membranes that are subjected to repetitive variations in pressure over long periods of time depends upon the membrane having elastomeric properties to withstand such repeated flexing without tearing or rupturing. Gas permeable membranes are not built to possess such elastomeric properties.

BRIEF SUMMARY OF THE INVENTION

The present invention provides a method and apparatus which allows one pressurized two liter "C" cylinder that contains 255 liters of oxygen at standard temperature and pressure to supply up to 34 hours of perfusion time and uses a simple electric pump driven by a storage battery to circulate the perfusion fluid through the organ being transported.

The device of the present invention is devoid of flexible membranes and instead uses flexible permeable tubing to oxygenate the perfusion fluid while the $CO_2$ produced by the organ diffuses out of the perfusion fluid.

The vessel containing the organ to be transported is held at 4° C. (39° F.) by coolant blocks.

All components are designed to use injection molding as the manufacturing method.

BRIEF DESCRIPTION OF THE SEVERAL VIEWS OF THE DRAWING

The advantages and features of the invention described herein can be understood in more detail by reference to the following description and drawings appended hereto and which form part of this specification.

The appended drawings illustrate a preferred embodiment of the invention and are therefore not to be considered limiting of its scope.

FIG. 5 is a cross-section view of the apparatus of the present invention taken along the lines 1B—1B of FIG. 3;

FIG. 5a is a detailed view of the lid-container sealing arrangement;

FIG. 5b is a perspective view of the adapter;

DETAILED DESCRIPTION OF THE INVENTION

Figure 1:
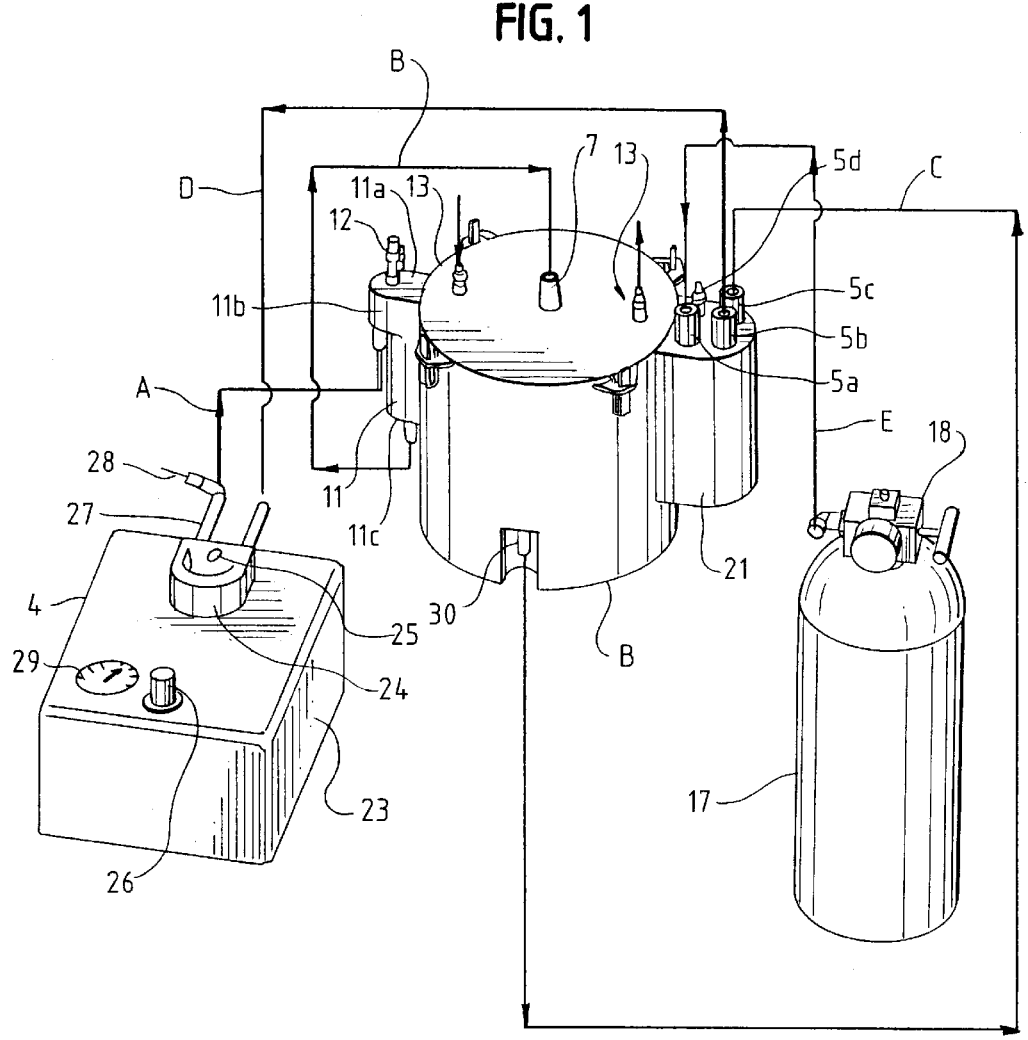
FIG. 1 is a hydraulic circuit diagram showing the interconnection of the principal components of a portable perfusion apparatus of the present invention.

As shown in FIG. 1, one embodiment of the perfusion apparatus of the present invention includes a compressed oxygen canister 17, an oxygenator chamber assembly 21, an organ container 8, an organ container lid 9, a bubble chamber 11, a pump assembly 4 and one or more cooling blocks or freezer packs 6.

The oxygen supply 17 is coupled to the oxygenator 21 through a pressure regulator 18. The oxygenator 21 is attached to the side of the reservoir or organ container 8. Similarly, the bubble chamber 11 is attached to the organ container 8 thus providing a compact assembly. The function and operation of the oxygenator 21 and the bubble chamber 11 will be described in more detail hereinafter.

Figure 3:
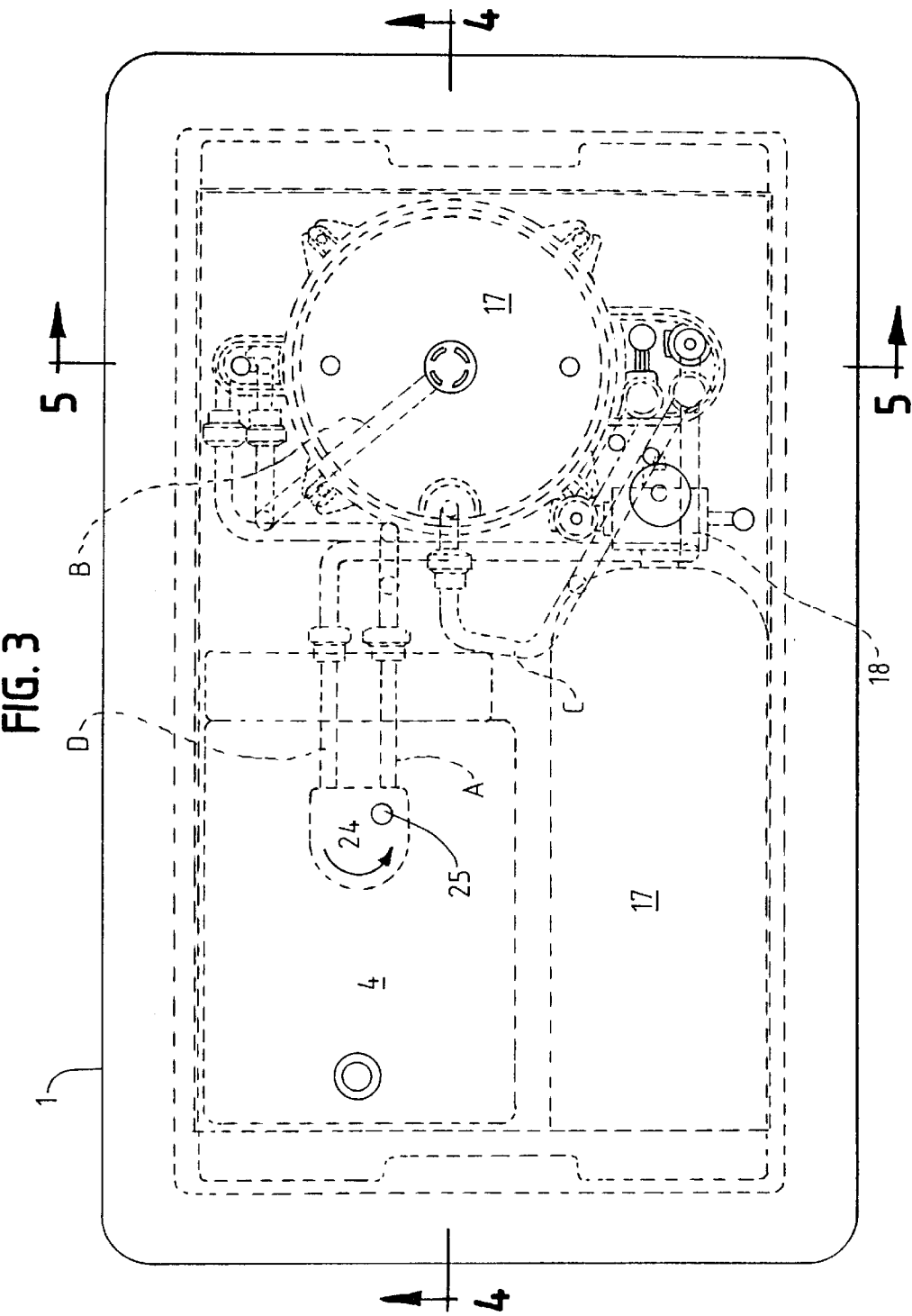
FIG. 3 is a plan view of the apparatus of the present invention.
Figure 4:
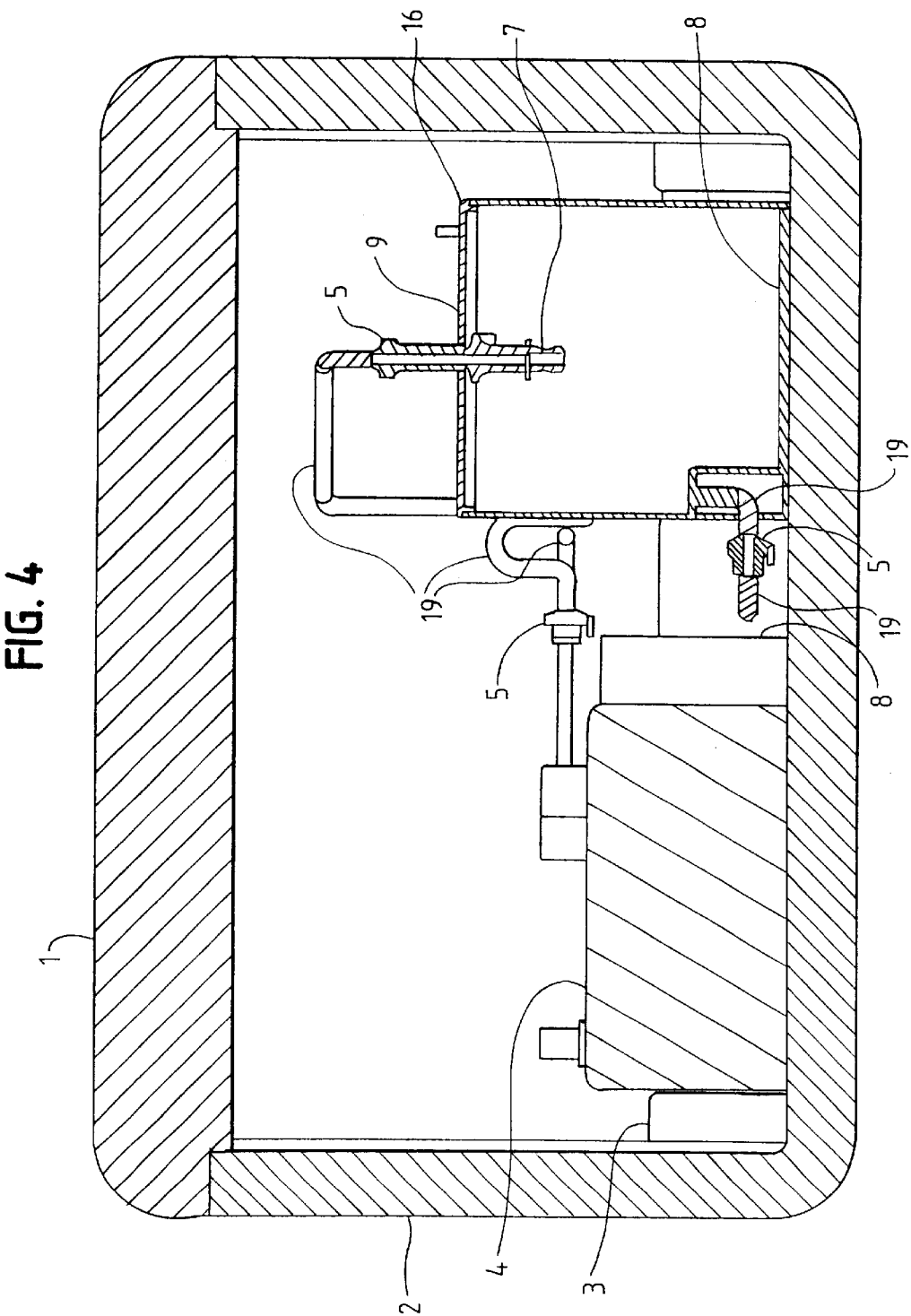
FIG. 4 is a cross-section view of the apparatus of the present invention taken along the lines 1A—1A of FIG. 3.
Figure 6:
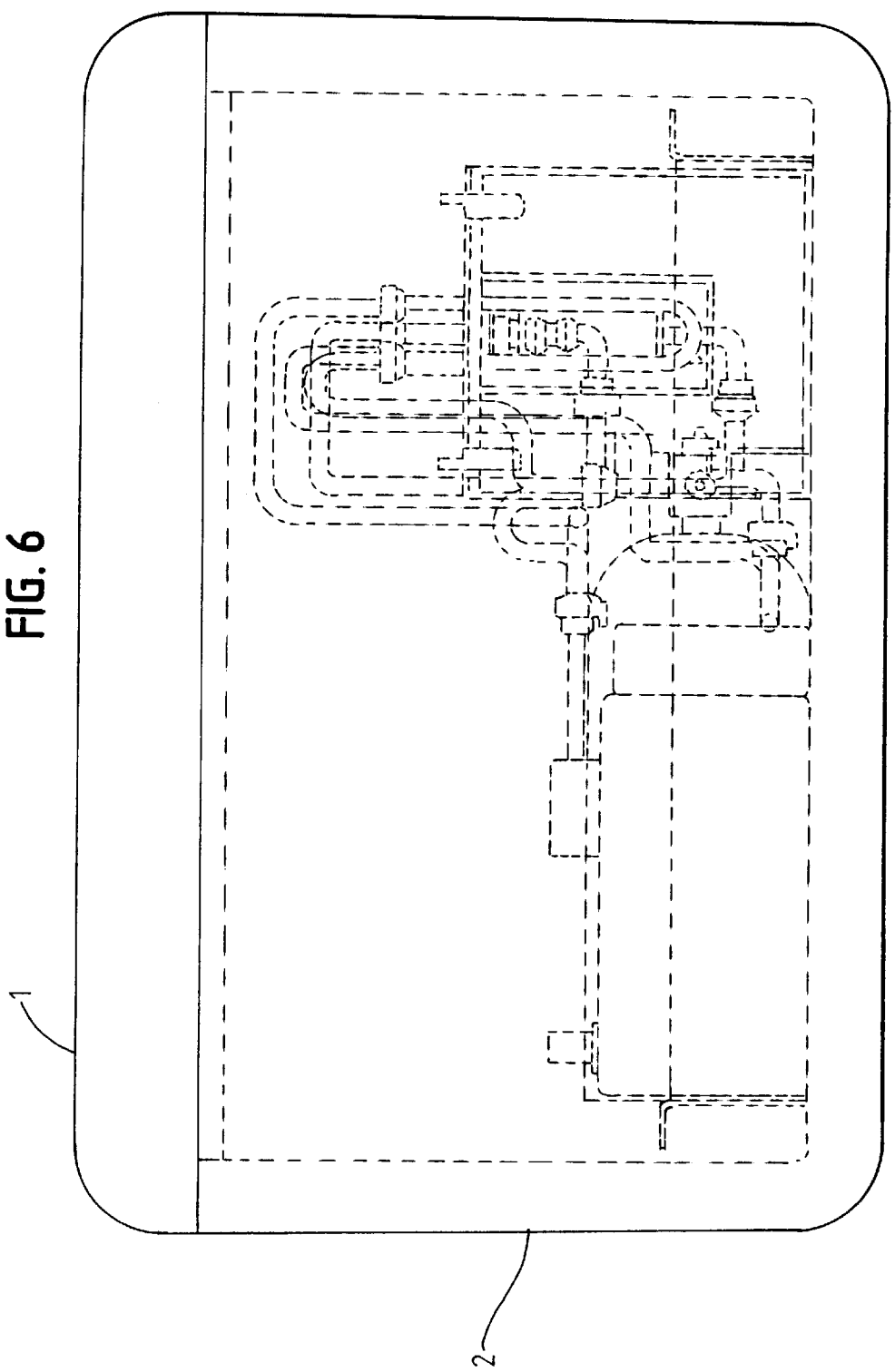
FIG. 6 is a sideview of the apparatus of the present invention.

As shown in FIG. 3, the organ container 8 together with the oxygenator assembly 21 and the bubble chamber 11 occupy approximately one third of a cooler 2 while the oxygen canister 17 together with the pump assembly 4 and cooling blocks 6 occupy the remainder of the cooler 2. The aforementioned components are mounted on a tray 3 as shown in FIG. 3. The cooler provides for a compact and readily transportable assembly of approximately 50 quarts. The weight of the entire assembly, including the organ to be transported and the perfusion fluid does not exceed 50 pounds.

Figure 2:
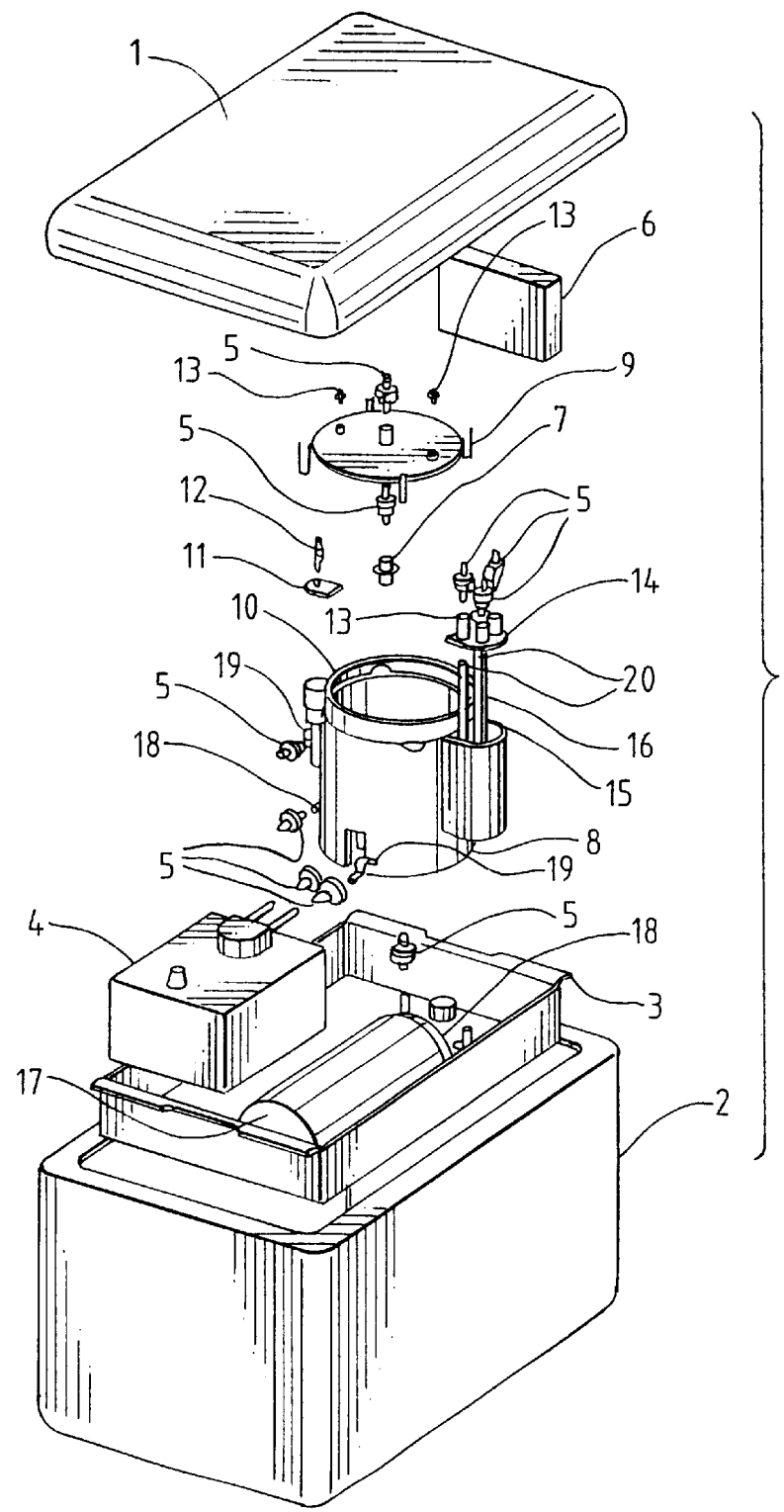
FIG. 2 is an expanded perspective view of the apparatus of the present invention.

FIG. 2 shows how the main components, in the oxygen canister 17, the oxygenator assembly 21, the organ container 8, the bubble chamber 11, the pump assembly 4 and cooling blocks 6 fit onto tray 3 and into the container 2.

The components are designed to be manufactured by injection molding using a polycarbonate resin such as Makralon® Rx-1805. This thermoplastic resin is a transparent polycarbonate formulated to provide increased resistance to chemical attack from intravenous (IV) fluids such as lipid emulsions.

The cover 9 for the organ container is sealed to the container 8 by means of a standard o-ring 10 as shown in FIG. 5a. Suitable fasteners are used to hold the cover 9 in place.

The cover 11a for the bubble chamber 11 and the cover 14 for the oxygenator 21 are glued in place using a U.V. cure adhesive.

The organ and perfusion fluid are thus sealed from the atmosphere and sterile conditions are maintained.

The tubing 19 used to connect the various components together is made from USC class 6, manufactured by many suppliers. Quick connect-disconnect couplings 5 are used throughout the assembly. One such fitting is manufactured by Colder Products and requires only one hand to operate. The fittings 5 are FDA approved and are readily available.

The assembly of the tubing 19 to the fittings 5 may be accomplished by pushing the tubing 19 onto tapered bosses 22. No barbs on the bosses are necessary due to the low pressure of the system. An alternative option would be to solvent bond or U.V. bond the tubing 19 to the tapered bosses 22.

Centrally located on the underside of the organ container cover or lid 9 is a standpipe or adaptor 7. This adaptor is connected to the bottom of cover 9 by means of a quick disconnect coupling 5. The adaptor is designed so that, for example, in case of a human heart the aorta may be attached to it.

While a cylindrical organ container is disclosed other cross-sections such as oval or rectangular may be used.

The oxygenator 21 is in the form of a hollow chamber with a cover 14 and is attached to the organ container 8. The cover 14 is equipped with 3 quick connect fittings 5a, 5b and 5c and one check valve 13 through which gases may be vented to the atmosphere. The quick connect fittings 5 are color coded so that improper connections may be avoided. Quick connect oxygen inlet fitting 5a communicates with the interior of the oygenator 21 by means of 4–6 gas permeable Silastic® tubes 22 through which oxygen is transferred to the perfusion fluid in the oxygenator 21. The flow of oxygen through the tubes is opposite to the direction in which the perfusion fluid flows through the oxygenator 21. This increases the efficiency of oxygen transfer to the fluid. The tubing is manufactured by Dow-Corning and is sold under catalog number 508-006. The tubing 22 has an inside diameter of 0.058 inches or 1.47 mm and an outside diameter of 0.077 inches or 1.96 mm. The oxygenator tubes are 24 inches long. Quick connect fittings 5b and 5c communicate with the interior of the oxygenator 21 and are used to supply used perfusion fluid for oxygenation through fitting 5c and withdraw oxygenated perfusion fluid through fitting 5b. Excess oxygen is bled to the atmosphere through check valve 5d so as to avoid foaming and bubbles in the perfusion fluid.

While our device uses a particular type of Silastic® tubing for gas exchange it should be understood that other silicone tubing or other materials may be used. For example, polyethylene is permeable to oxygen and carbon dioxide but not to aqueous solutions, it is, however, rigid. Thin polyethylene sheets can be used to make a functioning oxygenator in an assembly like an automobile radiator.

The bubble chamber 11 is in the form of a hollow chamber with a lid 11a. The chamber 11 has an upper portion 11b and a lower portion 11c. The cross-sectional area of the upper portion 11b of the chamber 11 is larger than the cross-sectional area of the lower portion 11c. The lower most portion of the upper and lower portions of the chamber 11 are provided with quick connect fittings 5 which communicate with the interior of the chamber 11. The cover 11a of the chamber 11 is equipped with a one-way stop cock 12 through which gasses are vented to the atmosphere.

It will be readily apparent to those skilled in the art that other forms of bubble chambers may be used such as one having a different cross-sectional area.

The pump assembly 24 comprises a box 23 which contains a sealed lead acid 12 volt battery 31, a DC brush motor 32 and an AC transformer 33 to supply 12 volt DC current to the motor when AC current is available. The motor shaft extends through the box 23 and drives the pump 24. The pump 24 is a peristaltic pump manufactured by APT Instruments and has a capacity of 8–10 milliliters/min/100 grams of organ weight. A human heart weighs approximately 450 grams. The pump 24 is mounted to the outside of the box 23 and the pump on-off switch 25 is mounted on the pump thus providing ready access. A pump r.p.m. gauge 26 is mounted on the outside of the box 23. Pump r.p.m. is an indication of flow rate of perfusion fluid. A pressure cuff 27 or pressure transducer 28 may be mounted on the fluid supply line A or inside a T-connection in case a pressure transducer is used. A pressure readout gauge 29 is mounted on the box 23. Appropriate pressure, temperature and fluid flow alarms (not shown) may be mounted on the box 23 or in another convenient location such as on the cooler 2.

Other forms of pumps may be advantageously used, for example, syringe pumps or centrifugal pumps may be readily substituted for the rotary roller pump disclosed.

The invention is useful for the transport of human organs such as the heart, kidneys, livers, lungs and the pancreas. The operation of the device will be described in connection with a human heart.

When a heart donor becomes available the surgeon removes the heart from the donor in the sterile environment of an operating room.

The tray 3 carrying the organ container 8 and the attached oxygenator 21 and bubble chamber 11 together with the pump assembly 4 and oxygen bottle 17 are present to receive the heart which is first emptied of blood with perfusion fluid. This is standard procedure. The aorta is then connected to the concave portion 7a of the adaptor 7. The heart is then suspended in the organ container 8 partially filled with perfusion fluid. The entire container 8 and the oxygenator 21 are then filled with fluid. The oxygen container 17 is connected to the oxygenator 21 by means of tube E.

The bottom of the organ container 8 has a perfusion fluid outlet 30 which is connected to the oxygenator inlet 5c by means of tube C so that used perfusion fluid can be transported to the oxygenator 21.

The outlet 5b of the oxygenator 21 is connected to the pump 24 by means of tube D so that oxygenated fluid can be pumped from the oxygenator 21 to the pump 24 and by means of tube A into the bubble chamber 11 where air bubbles and foam are removed from the fluid. Most of the bubbles form early during the course of perfusion.

From the bubble chamber the fluid travels from the bottom of the bubble chamber 11 through opening 31 through tube B into the adapter 7 to which the aorta has previously been sutured. The connection of the tube B to adapter 7 is the last connection made which assures that there is no air entering the aorta with the perfusion fluid.

The tray 3 is now placed in the cooler 2 and coolant blocks 6 are placed in the cooler to maintain the temperature in the cooler at approximately 4° C. to 6° C.

All connections of the tubes A–E are made with color-coded quick connect-disconnect fittings 5. Only one hand is needed to operate the fittings 5.

A heart is paralyzed just before it is harvested so that the donor heart is not contracting while being perfused. The oxygen requirements of a non-contracting heart cooled at 4° C. is $\frac{1}{100}$ of the oxygen consumed by an actively beating heart at body temperature (37° C). The two liter oxygen cylinder supplies 0.125 liter/minute oxygen for more than 34 hours, or over 160% of the amount needed to supply oxygen for a 24 hour period.

In our invention the rate of perfusion is controlled by controlling the r.p.m. of the pump 24. This may be accomplished by means of a pulse width modulator (PWM) which is a commercially available device.

It will thus be seen that we have provided for a portable organ transport device which will maintain the viability of an organ for at least 24 hours. The device is compact in construction and light in weight.

The entire assembly is housed in a commercial cooler holding approximately 50 quarts and the total weight is approximately 50 pounds.

The many benefits of our invention include the ability to deliver organs in better physiological condition, to shorten recovery times, to reduce overall cost, to increase the available time to improve tissue matching and sizing of the organ, to perform clinical chemistries and diagnostic testing for infectious diseases prior to transplantation, to enlarge selection of donor organs, to widen the range of available organs, to provide surgical teams with more predictable scheduling and relieving transplant centers of crisis management. Finally, the invention creates the feasibility of a worldwide network of donors and recipients.

What is claimed is:

1. An apparatus for transporting organs comprising
an organ container for receiving the organ to be transported,
a lid for said container to seal the container from the atmosphere,
an adapter extending through said lid and to which an organ may be attached,
said adapter being connected to a supply of perfusion fluid to perfuse the organ within said container,
a bubble chamber attached to said organ container for removing bubbles from said perfusion fluid,
an oxygenator assembly attached to said organ container for supplying oxygen to and removing carbon dioxide from said perfusion fluid,
said container, said bubble chamber and said oxygenator assembly providing a compact assembly for transportation of the organ.

2. The apparatus of claim 1 further including an oxygen container and a pump assembly, said oxygen container supplying oxygen to said oxygenator assembly, said pump assembly supplying oxygenated perfusion fluid to said organ.

3. The apparatus of claim 2 including a pressure regulator between said oxygen container and said oxygenator for regulating the amount of oxygen to the oxygenator assembly.

4. An apparatus for transporting organs comprising
an organ container for receiving the organ to be transported,
a lid for said container to seal the container from the atmosphere,
an adapter extending through said lid and to which an organ may be attached,
said adapter being connected to a supply of perfusion fluid to perfuse the organ within said container,
a bubble chamber attached to said organ container for removing bubbles from said perfusion fluid,
an oxygenator assembly attached to said organ container for supplying oxygen to and removing carbon dioxide from said perfusion fluid, said
oxygenator assembly including a plurality of tubes which are permeable to gas but not to liquid, said tubes being submerged in perfusion fluid so that oxygen supplied to the interior of said tubes migrates through the tubes and into the perfusion fluid,
an oxygen container and a pump assembly, said oxygen container supplying oxygen to said oxygenator assembly, said pump assembly supplying oxygenated perfusion fluid to said organ, and
a pressure regulator between said oxygen container and said oxygenator for regulating the amount of oxygen to the oxygenator assembly,
said container, said bubble chamber and said oxygenator assembly providing a compact assembly for transportation of the organ.

5. The apparatus of claim 1 including an o-ring between said lid and said container.

6. An apparatus for transporting organs comprising
an organ container for receiving the organ to be transported, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, a stop cock communicating with the upper portion of said bubble chamber through which gases may be vented to the atmospheres, an oxygenator assembly attached to said organ container for supplying oxygen to and removing carbon dioxide from said perfusion fluid, said oxygenator assembly including a plurality of tubes which are permeable to gas but not to liquid, said tubes being submerged in perfusion fluid so that oxygen supplied to the interior of said tubes migrates through the tubes and into the perfusion fluid, an oxygen container and a pump assembly, said oxygen container supplying oxygen to said oxygenator assembly, said pump assembly supplying oxygenated perfusion fluid to said organ, and a pressure regulator between said oxygen container and said oxygenator for regulating the amount of oxygen to the oxygenator assembly, said container, said bubble chamber and said oxygenator assembly providing a compact assembly for transportation of the organ.

7. An apparatus for transporting organs comprising an organ container for receiving the organ to be transported, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, an oxygenator assembly attached to said organ container for supplying oxygen to and removing carbon dioxide from said perfusion fluid, said container, said bubble chamber and said oxygenator assembly providing a compact assembly for transportation of the organ, in which the cross-sectional area of the upper portion of said bubble chamber is larger than the cross-sectional area of the lower portion of said bubble chamber.

8. An apparatus for transporting organs comprising an organ container for receiving the organ to be transported, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, an oxygenator assembly attached to said organ container for supplying oxygen to and removing carbon dioxide from said perfusion fluid, said container, said bubble chamber and said oxygenator assembly providing a compact assembly for transportation of the organ, an oxygen container supplying oxygen to said oxygenator assembly, and a pump assembly supplying oxygenated perfusion fluid to said organ, said pump assembly comprising a dc brush motor connected to a 12V dc battery for driving said pump.

9. The apparatus of claim 8 further including an on-off switch for said dc motor.

10. The apparatus of claim 9 including a pump r.p.m. control.

11. The apparatus of claim 10 in which said control is in the form of a pulse width modulator.

12. The apparatus of claim 10 including a box for receiving the battery, the motor and the transformer.

13. The apparatus of claim 10 in which the pump is mounted on the outside of the box and the drive shaft of the motor extends through a wall of the box for driving the pump.

14. The apparatus of claim 13 including means for visually displaying the pump r.p.m., the pump flow rate and the fluid pressure.

15. An apparatus for transporting organs comprising an organ container for receiving the organ to be transported, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, an oxygenator assembly attached to said organ container for supplying oxygen to and removing carbon dioxide from said perfusion fluid, an oxygen container supplying oxygen to said oxygenator assembly, a pump assembly, supplying oxygenated perfusion fluid to said organ, and plastic tubing and quick connect-disconnect couplings for connecting the organ container, the bubble chamber, the oxygenator, the pump assembly and the oxygen container, said apparatus providing a compact assembly for transportation of the organ.

16. The apparatus of claim 15 in which the couplings are color coded.

17. An apparatus for transporting organs comprising an organ container for receiving the organ to be transported, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, an oxygenator assembly attached to said organ container for supplying oxygen to and removing carbon dioxide from said perfusion fluid, an oxygen container supplying oxygen to said oxygenator assembly, a pump assembly supplying oxygenated perfusion fluid to said organ, and a tray for receiving said organ container together with said bubble chamber, said apparatus providing a compact assembly for transportation of the organ.

18. The apparatus of claim 17 in which said tray additionally carries said oxygen container and said pump assembly.

19. The apparatus of claim 17 or 18 in which said tray is contained in a cooler.

20. The apparatus of claim 19 in which said cooler is maintained at about 4° C.–6° C. by means of cooling blocks.

21. An apparatus for transporting organs comprising an organ container for receiving the organ to be transported, said organ container having an inlet and an outlet, a lid for said container to seal the container from the atmosphere, an adapter extending through said lid and to which an organ may be attached, said adapter being connected to a supply of perfusion fluid to perfuse the organ within said container, a bubble chamber attached to said organ container for removing bubbles from said perfusion fluid, said bubble chamber having a fluid inlet and a fluid outlet, an oxygenator assembly attached to said organ container, said oxygenator assembly comprising an oxygenator chamber for containing perfusion fluid, said oxygenator chamber having an inlet and an outlet, and oxygenator tubes within the chamber for supplying oxygen to and removing carbon dioxide from said perfusion fluid, said oxygenator tubes having inlets and outlets, an oxygen container connected to the oxygenator tubes of the oxygenator and supplying oxygen to said oxygenator assembly, and a pump assembly supplying oxygenated perfusion fluid to said organ, said pump assembly having a fluid inlet and a fluid outlet, wherein the oxygen container is connected to the inlets of the oxygenator tubes, the organ container outlet is connected to the oxygenator chamber, the organ container inlet is connected to the outlet of the bubble chamber, the oxygenator fluid outlet is connected to the pump inlet, the pump outlet is connected to the bubble chamber inlet and the bubble chamber outlet is connected to the adapter, said apparatus providing a compact assembly for transportation of the organ.

22. The apparatus of claim 1, having a weight not exceeding 50 pounds when in use.

23. The apparatus of claim 1, having at least two components connected by tubing and quick connect-disconnect couplings.

24. The apparatus of claim 1, operated at a low pressure.

25. The apparatus of claim 1, wherein said oxygenator assembly includes a plurality of tubes which are permeable to gas but not to liquid, said tubes being submerged in perfusion fluid during use so that oxygen supplied to the interior of said tubes migrates through the tubes and into the perfusion fluid.

* * * * *